(12) United States Patent
Martin (10) Patent No.: US 6,893,413 B2
(45) Date of Patent: May 17, 2005

(54) TWO-PIECE STENT COMBINATION FOR PERCUTANEOUS ARTERIALIZATION OF THE CORONARY SINUS AND RETROGRADE PERFUSION OF THE MYOCARDIUM

(76) Inventor: Eric C. Martin, 134 Old Post Rd., Croton On Hudson, NY (US) 10520

( * ) Notice: Subject to any disclaimer, the term of this patent is extended or adjusted under 35 U.S.C. 154(b) by 468 days.

(21) Appl. No.: 10/036,441

(22) Filed: Jan. 7, 2002

(65) Prior Publication Data

US 2003/0130611 A1 Jul. 10, 2003

(51) Int. Cl.$^7$ .............................. A61M 5/00; A61F 2/06
(52) U.S. Cl. ........................... 604/8; 604/264; 623/1.11
(58) Field of Search ............................. 604/8–10, 6.16, 604/157, 264, 247; 623/1.1–1.15, 1.23, 1.24, 1.3; 600/16

(56) References Cited

U.S. PATENT DOCUMENTS

| | | | |
|---|---|---|---|
| 2,127,903 A | | 8/1938 | Bowen |
| 5,180,392 A | | 1/1993 | Skeie et al. |
| 5,287,861 A | | 2/1994 | Wilk |
| 5,380,316 A | | 1/1995 | Aita et al. |
| 5,389,096 A | | 2/1995 | Aita et al. |
| 5,409,019 A | | 4/1995 | Wilk |
| 5,429,144 A | | 7/1995 | Wilk |
| 5,549,581 A | | 8/1996 | Lurie et al. |
| 5,653,743 A | | 8/1997 | Martin |
| 5,655,548 A | | 8/1997 | Nelson et al. |
| 5,667,486 A | | 9/1997 | Mikulich et al. |
| 5,755,682 A | * | 5/1998 | Knudson et al. .............. 604/8 |
| 5,824,071 A | * | 10/1998 | Nelson et al. .............. 606/194 |
| 5,897,588 A | | 4/1999 | Hull et al. |
| 6,010,530 A | | 1/2000 | Goicoechea |
| 6,015,432 A | | 1/2000 | Rakos et al. |
| 6,017,365 A | | 1/2000 | Von Oepen |
| 6,027,526 A | * | 2/2000 | Limon et al. .............. 623/1.15 |
| 6,053,942 A | | 4/2000 | Eno et al. |
| 6,149,682 A | | 11/2000 | Frid |
| 6,190,406 B1 | * | 2/2001 | Duerig et al. ................ 623/1.2 |
| 6,258,120 B1 | | 7/2001 | McKenzie et al. |
| 6,371,981 B1 | | 4/2002 | Yang et al. |
| 6,395,021 B1 | | 5/2002 | Hart et al. |
| 6,562,066 B1 | | 5/2003 | Martin |
| 6,605,053 B1 | * | 8/2003 | Kamm et al. ................... 604/8 |

OTHER PUBLICATIONS

Gensini, G.G., et al., Anatomy of the Coronary Circulation in Living Man, Circulation, May 1965, pp. 778–784, vol. XXXI.

Eckstein, R.W., et al., Acute Effects of Elevation of Coronary Sinus Pressure, Circulation, Mar. 1953, pp. 422–436, vol. VII.

Gardner, R.S., et al., Arterialization of Coronary Veins in the Treatment of Myocardial Ischemia, The Journal of Thoracic and Cardiovascular Surgery, Aug. 1974, pp. 273–282, vol. 68, No. 2.

Zajtchuk, R., et al., Revascularization of the Hearth through Coronary Veins, The Annals of Thoracic Surgery, Apr. 1976, pp. 318–321, vol. 2, No. 4.

Patel, N.H., et al., Percutaneous Transmyocardial Intracardiac Retroperfusion Shunts: Technical Feasibility in a Canine Model, Journal of Vascular and Interventional Radiology, Mar. 2000, pp. 382–390, vol. 11, No. 3.

(Continued)

Primary Examiner—Angela D. Sykes
Assistant Examiner—Leslie Deak
(74) Attorney, Agent, or Firm—Milbank, Tweed, Hadley and McCloy LLP (57) ABSTRACT

The present invention contemplates a method for percutaneously providing oxygenated blood retrogradely from the left ventricle via coronary sinus to the heart tissue without a significant left-to-right shunt. The present invention contemplates a two-piece stent combination generally having an arterializing stent and a restricting covered stent.

36 Claims, 6 Drawing Sheets

OTHER PUBLICATIONS

Rosch, J., et al., Coaxial Catheter–Needle System for Transjugular Portal Vein Entrance, Journal of Vascular and Interventional Radiology, Jan.–Feb. 1993, pp. 145–147, vol. 4.

Schofield, P.M., et al., Transmyocardial Laser Revacularisation in Patients with Refractory Angina: A Randomised Controlled Trial, The Lancet, Feb. 13, 1999, pp. 519–524, vol. 353.

Horvath, K.A., et al., Transmyocardial Laser Revascularization: Results of a Multicenter Trial with Transmyocardial Laser Revascularization Used as Sole Therapy for EndStage Coronary Artery Disease, The Journal of Thoracic and Cardiovascular Surgery, Apr. 1997, pp. 645–653, vol., 113, No. 4.

Mohl, W., The Momentum of Coronary Sinus Interventions Clinically, Circulation, Jan. 1988, pp. 6–12, vol. 77, No. 1.

Mohl, W., The Relevance of Coronary Sinus Interventions in Cardiac Surgery, Thorac. Cardiovasc. Surgeon, 1991, pp., 245–250, vol. 39.

Kar, S., et al., Coronary Veins: An alternate Route to Ischemic Myocardium, Heart & Lung, Mar. 1992, pp. 148–157, vol. 21, No. 2.

Meerbaum, S., et al., Diastolic Retroperfusion of Acutely Ischemic Myocardium, The American Journal of Cardiology, Mar. 31, 1976, pp. 588–598, vol. 37.

Park, S.B., et al., Direct Selective Myocardial Revascularization by Internal Mammary Artery–Coronary Vein Anastomosis, The Journal of Thoracic and Cardiovascular Surgery, Jan. 1975, pp. 63–72, vol. 69, No. 1.

Eckstein, R.W., et al., Chronic Effects of Aorta–Coronary Sinus Anastomosis of Beck in Dogs, Circulation Research, Jan. 1954, pp. 60–72., vol. 11.

* cited by examiner

TWO-PIECE STENT COMBINATION FOR PERCUTANEOUS ARTERIALIZATION OF THE CORONARY SINUS AND RETROGRADE PERFUSION OF THE MYOCARDIUM

BACKGROUND

I. Field of Invention

The present invention concerns a two-piece stent combination for supplying oxygenated blood retrogradely from the left ventricle to the myocardium via the coronary sinus. It has an arterializing stent, which directs blood from the left ventricle to the coronary sinus, and a restricting covered stent, which controls the amount of blood flowing from the coronary sinus into the right atrium and thereby directing blood retrogradely to the myocardium.

II. Description of Related Technology

Retrograde perfusion of the heart through the coronary sinus has long been known for treating end-stage heart disease. Previous methods, among others, have attempted to connect the aorta to the coronary sinus during open-heart surgery using a graft of the jugular vein, the internal mammary artery, or the carotid artery. Alternatively, an occlusion balloon has been used for a short period of time.

Nelson et al. (U.S. Pat. No. 5,824,071, 1998) discloses an apparatus and method for providing retrograde perfusion directly from the left ventricle to the coronary sinus. Although Nelson requires a pressure sensitive valve that prevents pressure build-up inside the coronary sinus from rising above 60 mm Hg, Nelson does not teach how such a valve may be constructed. Nelson does not teach or describe the features or components of such a pressure sensitive valve. Further, it is unlikely that such a device may be introduced percutaneously and will likely require invasive surgery.

In 2000, Patel et al. conducted an experiment for percutaneous arterialization of the coronary sinus using a stent. See Patel et al, *Percutaneous Transmyocardial Intracardiac Retroperfusion Shunts: Technical Feasibility in a Canine Model,* JVIR 2000, 11:382–390. The stent employed by Patel et al., however, results in a significant amount of shunting of oxygenated blood from the left ventricle to the right atrium (hereinafter "left-to-right shunt"). These shortcomings in the prior art are solved by the present invention.

SUMMARY OF INVENTION

The present invention incorporates by reference application Ser. No. 09/796,528, titled A STENT FOR ARTERIALIZATION OF CORONARY SINUS AND RETROGRADE PERFUSION OF THE MYOCARDIUM, filed Mar. 2, 2001, and application Ser. No. 10/036,445, titled A BIFURCATED STENT FOR ARTERIALIZATION OF THE CORONARY SINUS AND RETROGRADE PERFUSION OF THE MYOCARDIUM, filed Jan. 7, 2002.

The present invention contemplates a method for percutaneously providing oxygenated blood retrogradely from the left ventricle via the coronary sinus to the heart tissue without a significant left-to-right shunt. The present invention contemplates a two-piece stent combination generally having an arterializing stent and a restricting covered stent. The arterilializing stent and the restricting covered stent may optionally be connected, e.g., by a connecting wire. The arterializing stent allows aterialized blood from the left ventricle to flow directly into the coronary sinus. The arterilizing stent is fitted and expanded within a hole punctured through the coronary sinus and the wall of the left ventricle to allow fluid passageway between the left ventricle and the coronary sinus. The restricting covered stent, which is positioned so that it fits securely within the the coronary sinus, controls the amount of blood flowing from the coronary sinus into the right atrium and therefore controls the left-to-right shunt and the amount of retrograde flow to the mycardium.

In the two-piece stent combination, the arterilizing stent has preferably a tubular shape with a passageway therethrough with a leading end and a trailing end. After a hole is created percutaneously through the heart wall and the wall of the coronary sinus, the arterializing stent is delivered to fit within that hole and to provide fluid communication between the left ventricle and the coronary sinus, with the leading end positioned within the left ventricle and the trailing end positioned within the coronary sinus. The arterializing stent may have a variety of shapes. In one embodiment, it has a tubular shape that increases in cross-sectional diameter from the leading end to the trailing end. In another embodiment, the stent has a constant cross-sectional area along its extent. And finally, the stent may also have a constriction, which is preferably near the leading end, with the cross-sectional diameter tapering down toward the constriction. The arterilizing stent may optionally be covered with a covering.

The two-piece stent combination also has a restricting covered stent, which may further have an underlying restriction stent and a covering. The restricting covered stent generally has a tubular shape with a coronary sinus ("CS") end and a right atrial ("RA") end, with the CS end positioned in the coronary sinus and the RA end positioned in the right atrium. The restricting covered stent also may have a constriction, or a decreased cross-sectional area, in its mid portion, preferably nearer to the RA end. Thus, the restricting covered stent can generally be divided into two portions: the CS portion and the RA portion. The cross-sectional diameter of the restricting covered stent increases from the constriction portion toward the two ends, the CS end and the RA end.

The present invention also contemplates delivering the two-piece stent combination percutaneously. After the arterializing stent is percutaneously delivered within the hole [over a wire guide], the arterializing stent is preferably expanded using a balloon or self expands to achieve its desired diameter. The restricting covered stent is then delivered percutaneously to be positioned so that the constriction fits within the coronary ostium, with the CS portion fitting substantially within the coronary sinus and the RA portion fitting substantially within the right atrium. In alternative embodiments, the constriction may be within the coronary sinus. In another embodiment, the RA portion may also be within the coronary sinus. After delivery of the restricting covered stent, the CS portion of the restricting covered stent generally expands to fill the coronary sinus and to form a friction fit. Suitable material for the covering include, among others, PET and PTFE.

The underlying arterializing stent and the underlying restricting stent are made of flexible material such as steel or nitinol that allow compression or expansion cross-sectionally. For example, each may be compressed to fit within a delivery catheter for percutaneous delivery into their desired position. And after delivery, the arterializing stent and the restricting covered stent may self expand or may be expanded using a balloon as known in the art. Generally, the arterializing stent is delivered first, followed by the delivery of the restricting covered stent. To facilitate the positioning of these stents, they are preferably marked with a radio-opaque material, such as platinum or gold. For example, the arterializing stent may include radio-opaque rings at the leading end and at the trailing end. Also, the restricting covered stent may include radio-opaque rings about the constriction, at the CS end, and/or at the RA end for fluoroscopic control.

Blood flows from the left ventricle into the coronary sinus by flowing through the leading end of the arterializing stent and out of its trailing end. Once inside the coronary sinus, blood may flow in either or both directions. Blood may flow out of the coronary sinus to the right atrium by flowing through the CS end, the passageway, and the RA end of the restricting covered stent. Or blood may flow retrogradely through the coronary sinus to the myocardium.

The size of the passageway in the arterilizing stent controls the amount of blood flowing into the coronary sinus from the right atrium. The size of the constriction in the restricting covered stent controls the amount of blood flowing out of the coronary sinus into the right atrium. By diminishing the amount of left-to-right shunt, the pressure in the coronary sinus is increased and blood is increasingly directed to the myocardium retrogradely through the retrograde portion of the coronary sinus. Some amount of blood flow into the right atrium, however, is necessary to control the pressure in the coronary sinus. The diameter of the passageway at the constriction should thus be large enough to prevent the pressure inside the coronary sinus from rising above a suitable level, e.g., about 50 mm Hg or otherwise about half of systemic pressure. But at the same time, the diameter of the constriction should also be small enough to avoid excessive or deleterious left-to-right shunting. In other words, the amount of left-to-right shunting preferably does not create a significant strain on the heart. As an illustrative example only, and not as a limitation, the amount may preferably be less than approximately a one-and-a-half to one shunt ratio. These features will also be dependent on the diameter of the arterializing stent, which controls the inflow into the coronary sinus. Thus, the diameters are interdependent.

DETAILED DESCRIPTION

The two-piece stent combination of the present invention has an arterializing stent and a restricting covered stent. In one embodiment, the arterializing stent and the restricting covered stent are placed in their desired positions and are not connected. In another embodiment, however, the arterializing stent may be connected to the restricting covered stent, e.g., by a wire.

Figure 1:
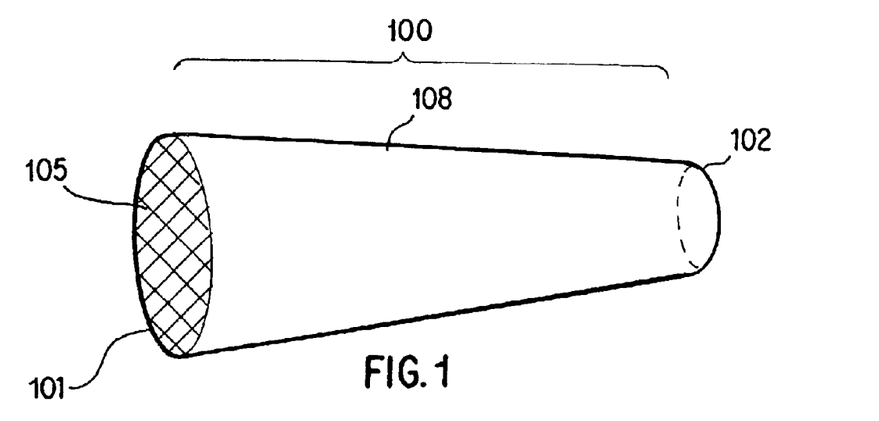
FIG. 1 shows an embodiment of an arterializing stent, wherein the cross-sectional diameter tapers from the trailing end to the leading end.

A preferred embodiment of the arterializing stent 100 according to the present invention is illustrated in FIG. 1. The arterializing stent 100 generally has an underlying arterilizing stent 105 and an optional covering 108. The arterializing stent 100 has a leading end 102, which is placed in the left ventricle, and a trailing end 101, which is placed in the coronary sinus. The arterializing stent 100 generally has a tubular shape with a passageway therethrough.

Figure 2:
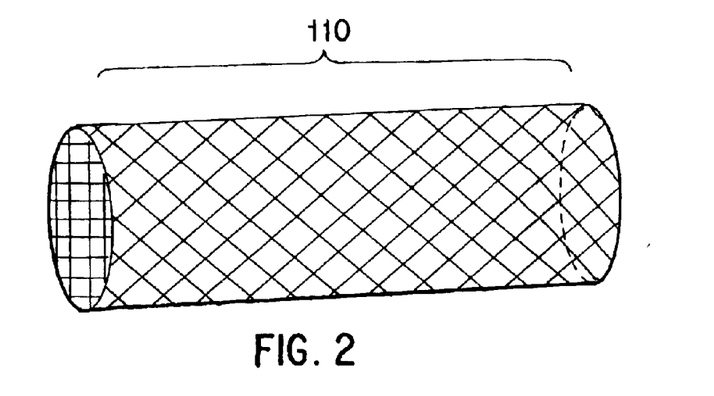
FIG. 2 shows another embodiment of an arterializing stent, wherein the cross-sectional diameter is constant along its extent.
Figure 3:
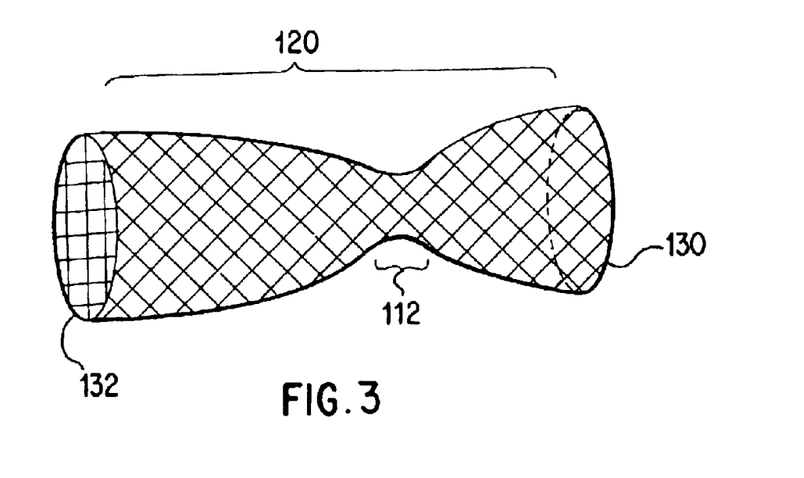
FIG. 3 shows another embodiment of an arterializing stent having a constriction, which may be anywhere along its length, but preferably near the leading end or the middle.

Referring to FIGS. 1–3, the shape of the arterializing stent may be one of a variety of shapes. In one embodiment, as seen in FIG. 1, it has a tubular shape with a cross-sectional diameter that tapers or decreases from the trailing end 101 to the leading end 102. In another embodiment, as seen in FIG. 2, the tubular shape has a constant cross-sectional diameter along its extent. In yet another embodiment, as seen in FIG. 3, the tubular shape has a constriction 112 anywhere along its tubular length, but preferably near the leading end or the middle, with the cross-sectional diameter being the smallest at the constriction 112. Depending on configuration and need, these arterializing stents may or may not be covered.

Thus, as seen in FIG. 1, the underlying arterializing stent 105 may be covered with an optional covering 108. The optional covering 108 is preferably inside the underlying arterializing stent 105, but may also be outside. In yet another embodiment, the underlying arterializing stent 105 may be sandwiched between an outer and an inner covering. The covering 108 is preferably made from any of a number of commercially available materials such as PET, PTFE, or any other suitable material as known in the art.

Figure 4:
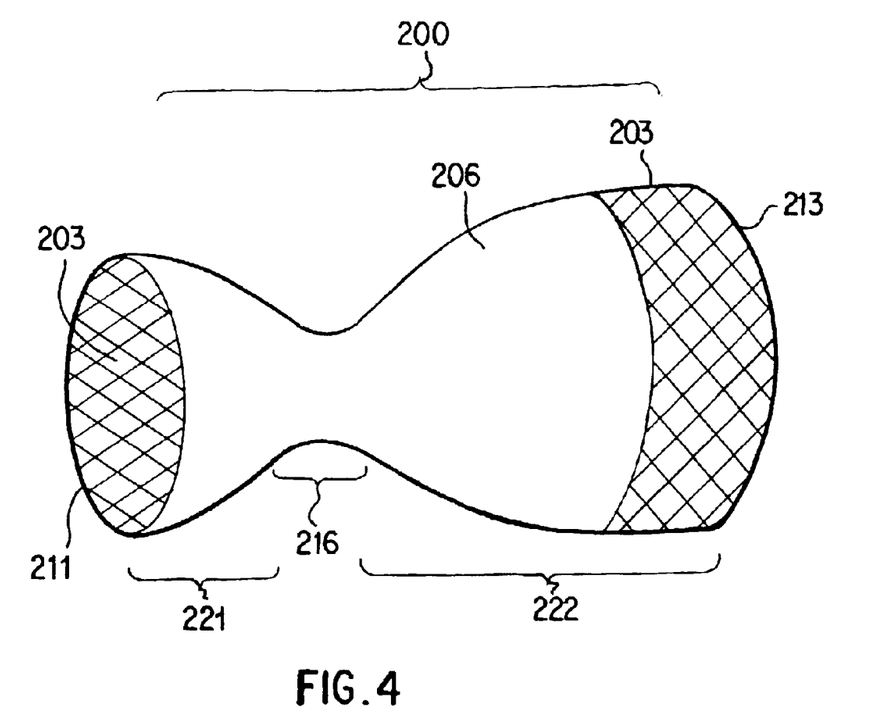
FIG. 4 shows an embodiment of a restricting covered stent, wherein the covering covers a portion of the CS portion of the underlying restricting stent.

The two-piece stent combination according to the present invention also has a restricting covered stent 200 as seen in FIG. 4. The restricting covered stent 200 generally has an underlying restricting stent 203 and a covering 206. The covering 206 may be either inside or outside the underlying restricting stent 203 or both inside and outside. The covering 206 is also made from any of a number of commercially available material such as PET, PTFE, or other suitable material known in the art. Hereinafter, the combination of the underlying restricting stent 203 and the covering 206 will be referred to as restricting covered stent 200.

The restricting covered stent 200 generally has a tubular shape with a passageway therethrough with a coronary sinus ("CS") end 213 and a right atrial ("RA") end 211. The restricting covered stent 200 also has a constriction 216 between the RA end 211 and the CS end 213, wherein the cross-sectional diameter at the constriction 216 is the smallest. The constriction 216 is preferably near the middle or nearer to the RA end 211. The cross-sectional diameter of the restricting covered stent 200 tapers toward the constriction 216. The body of the restricting covered stent 200 may generally have the RA portion 221 and the CS portion 222.

Figure 5:
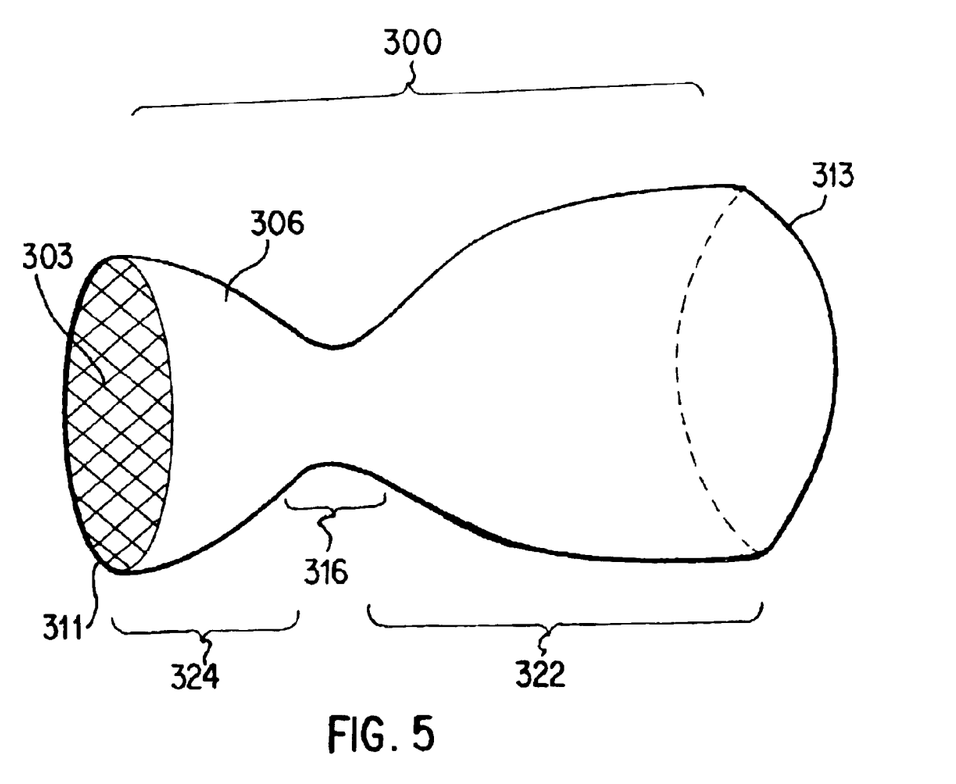
FIG. 5 shows an embodiment of a restricting covered stent, wherein the covering covers the entire CS portion of the underlying restricting stent.

In the embodiment shown in FIG. 4, the covering 206 does not cover the entire CS portion 222 of the underlying restricting stent 203. In an alternative embodiment shown in FIG. 5, the covering 306 covers the entire CS portion 322 of the underlying restricting stent 303.

The underlying arterializing stent 105 of FIG. 1 and the underlying restricting stent 203 of FIG. 2 are preferably made of a flexible material that can withstand bending without kinking to allow fluid passageway therethrough. A number of suitable commercially available stents with these desired characteristics may be employed in practicing the present invention. Metallic stents as well as non-metallic stents may be used in the construction. For example, metallic material may be surgical grade stainless steel or nitinol. Non-metallic stents, for example, may be made of a suitable plastic material. Suitable designs include various wire mesh designs and weave configurations as known in the art. In one embodiment, these underlying stents 105 and 203 may have a coiled construction as known in the art.

These underlying stents 105 and 203 are preferably made of flexible material that allows bending without kinking to allow a fluid passageway to be maintained. Furthermore, these underlying stents 105 and 203 also allow compression and expansion cross-sectionally to fit within a delivery cathether and for expansion after delivery. These underlying stents 105 and 203 preferably self expand or may be expanded using a balloon as known in the art.

In a preferred embodiment, the lengths of the arterilizing stents 100, 110, and 120 of FIGS. 1–3 are from about 1 cm to about 4 cm. In FIG. 1, the cross-sectional diameter at the leading end 102 is smaller than the cross-sectional diameter at the trailing end 101. The cross-sectional diameter at the leading end 102 is preferably from about 2 mm to about 5 mm, and the cross-sectional diameter at the trailing end 101 is preferably from about 4 mm to about 6 mm. In FIG. 2, the cross-sectional diameter is constant throughout the length of the arterializing stent 110, preferably from about 1 mm to 6 mm, and more preferably from about 2 mm to about 5 mm. And in FIG. 3, the cross-sectional diameter of the arterializing stent 120 tapers toward the constriction 112, with the smallest cross-sectional diameter at the constriction 112. The preferred cross-sectional diameter at the leading end 130 is from about 1 mm to about 6 mm and more preferably from about 2 mm to about 5 mm; at the trailing end 132, is from about 1 mm to about 6 mm; and more preferably from about 2 mm to about 5 mm, and at the constriction 112, is from about 2 mm to about 5 mm.

For the restricting covered stent 200 of FIG. 4, the cross-sectional diameter at the constriction 216 is preferably from about 1 mm to about 6 mm, and more preferably from about 2 mm to about 5 mm. The cross-sectional diameter tapers toward the constriction 216. The CS end 213 and the RA end 211 of the restricting covered stent 200 have a preferable cross-sectional diameter from about 6 mm to about 15 mm. Furthermore, restricting covered stent 200 has a length preferably from about 1 cm to about 4 cm. The length of the RA portion 221 is preferably from about 0.5 cm to about 1.5 cm, and the length of the CS portion 222 is preferably from about 0.5 to about 2.0 cm.

Figure 6:
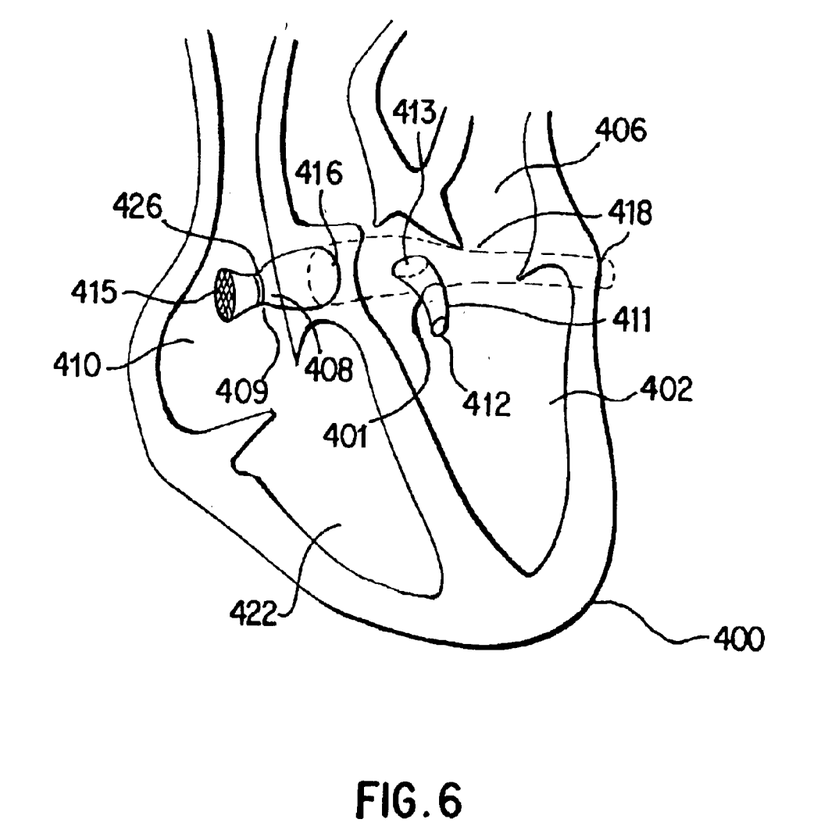
FIG. 6 shows a preferred placement of the two-piece stent combination according to the present invention in a schematic diagram of the heart.

Referring now to FIG. 6, the two-piece stent combination having the restricting covered stent 408 and arterializing stent 411 is positioned in a schematic diagram of the human heart 400. The heart 400 generally has a left ventricle 402, a left atrium 406, a right ventricle 422, and a right atrium 410. The left atrium 406 receives oxygenated blood from the lungs, which is then delivered to the left ventricle 402, which is primarily responsible for delivering oxygenated blood to the body. The right atrium 410 is primarily responsible for receiving deoxygenated blood from the body. Deoxygenated blood then flows into the right ventricle 422 before being sent to the lungs for oxygenation. After perfusing the heart, oxygenated blood from the coronary arteries normally drains to the coronary sinus 418 and into the right atrium 410. The coronary ostium 426 connects the coronary sinus 418 to the right atrium 410.

Figure 7:
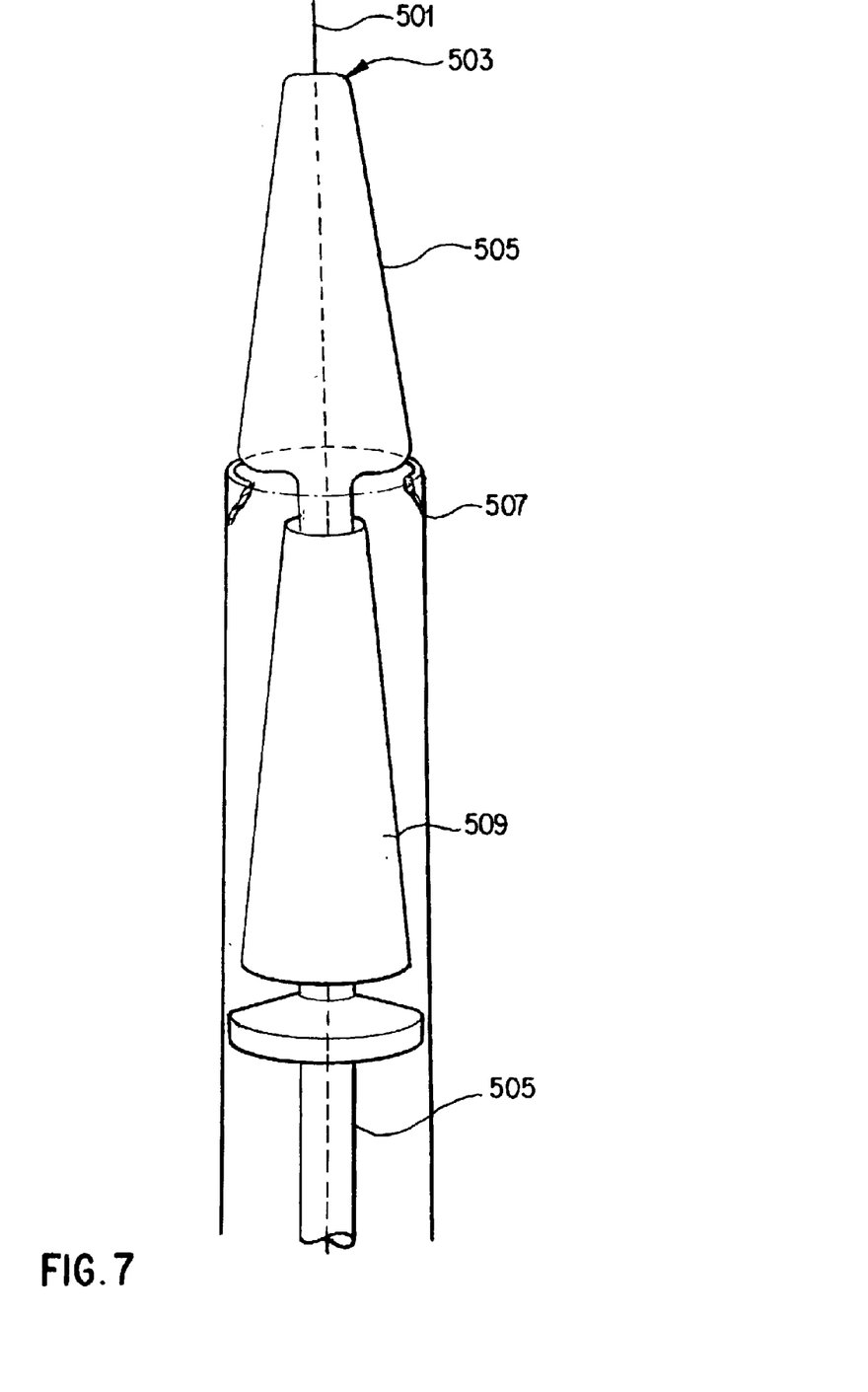
FIG. 7 shows an apparatus for percutaneously delivering the arterializing stent.
Figure 8:
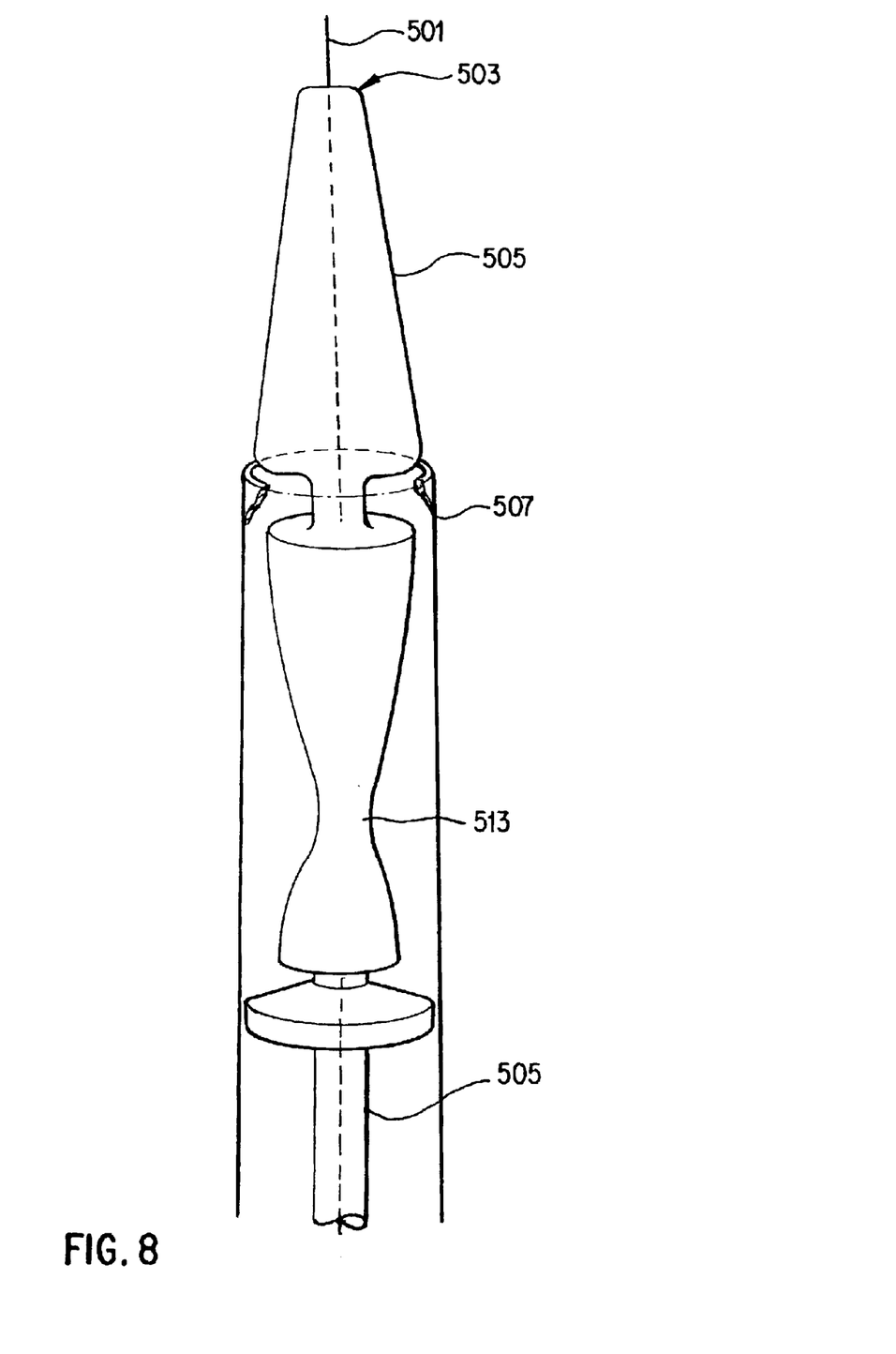
FIG. 8 shows an apparatus for percutaneously delivering the restricting covered stent.

For delivering the invention, in a preferred embodiment as shown in FIGS. 7 and 8, the arterializing stent 509 and/or a restricting covered stent 513 may be compressed around a catheter and covered by a retractable sheath 507 to be introduced and placed into position before retracting the sheath to release the stent. If the arterializing stent 411 and the restricting covered stent 408 are connected by a wire (not pictured), the two stents 411 and 408 may be delivered using a single catheter. The method used by Patel et al. may be employed in delivering the stent according to present invention or as known as in the art. Patel et al., *Percutaneous Transmyocardial Intracardiac Retroperfusion Shunts: Technical Feasibility in a Canine Model*, JVIR 2000, 11:382–390. Patel, et al. modifies the stent delivery method as described by Rosch, et al. in Rosch, et al., *Coaxial Catheter Needle System for Transjugular Portal Vein Entrance*, JVIR, Vol. 4, No. 1, pp. 145–147, 1993.

Referring back to FIG. 6, a sheath is introduced into the jugular vein percutaneously, through which the coronary sinus 418 is catheterized and a wire is introduced. Once the catheter is removed, a stiff needle guide combination is passed over the wire as known in the art. The needle guide is aimed at the left ventricle 402 (marked with a percutaneously introduced pigtail catheter) and pierced through the coronary sinus wall into the left ventricle 402. A guide wire is passed into the aorta (not pictured) and the needle guide is removed to leave a hole 401. The hole 401 punctured allows for the arterializing stent 411 to fit therebetween. The arterializing stent 411 may then be widened using a balloon catheter as known in the art to allow blood to flow from the left ventricle 402 into the passageway of the arterializing stent 411 and into the coronary sinus 418.

Delivery involves first delivering the arterializing stent 411 followed by delivering the restricting covered stent 408. Either or both the arterializing stent 411 and the restricting covered stent 408 is placed within the retractable sheath 507 of the catheter 505. Catheter 505 also has a tip 503 which is guided by the guide wire 501. The catheters are preferably pre-loaded with either the arterializing stent 411 and/or the restricting covered stent 408. After positioning, the retractable sheath 507 of the catheter 505 is retracted, and either the arterializing stent 411 and/or the restricting covered stent 408, which is preferably preloaded, is allowed to expand if self expanding. Furthermore, a catheter (not pictured) placed in the coronary sinus 218 for contrast injection may aid in aligning with the coronary sinus 218.

To facilitate delivery, radio-opaque rings (not pictured) may be placed on either the arterializing stent 100 or the restricting covered stent 200. Referring back to FIG. 1, radio-opaque rings may be placed at the trailing end 101 and/or at the leading end 102 of the arterializing stent 100. In FIG. 3, radio-opaque rings may be placed at the trailing end 132, the constriction 112, and/or the leading end 130 of the arterializing stent 120. Likewise, referring to FIG. 4, radio-opaque rings may be placed at the RA end 211, constriction 216, and/or the CS end 213 of the restricting covered stent 200. The radio-opaque rings facilitate fluoroscopic viewing for guidance during delivery.

Upon delivery, referring again to FIG. 6, the arterializing stent 411 is preferably positioned so that its leading end 412 is positioned within the left ventricle 202 and the trailing end 413 is positioned within the coronary sinus 418. The restricting covered stent 408 is preferably positioned so that its CS end 416 is positioned within the coronary sinus. Preferably, the RA end 415 is positioned within the right atrium 410. Also preferably, the constriction 409 preferably fits approximately within the coronary ostium 426 to make a secure fit.

In an alternative embodiment, the RA end and/or the constriction may be located within the coronary sinus. After delivery, either through self-expansion or assisted expansion as known in the art, the RA portion of the restricting covered stent 408 forms a friction fit with the interior of the coronary sinus 418.

The amount of blood flow to the retrograde portion of the coronary sinus 418 is generally inversely related to the amount of left-to-right shunting. Blood in the coronary sinus 418 flows either through the restricting covered stent 408 into the right atrium 410 or to the retrograde portion of the coronary sinus 418 to provide retrograde perfusion to the myocardium. There may also be some amount of blood flowing back into the left ventricle 402. Generally, the smallest cross sectional diameter of the restricting covered stent 408, which is usually at the constriction, influences the amount of left-to-right shunt. For example, decreasing the size of the passageway at the constriction 409 increases the retrograde perfusion of the myocardium. Thus, if the size of the passageway at the constriction 409 and therefore the rate of blood flow into the right atrium 410 is too great, the heart tissue would not adequately be perfused. Furthermore, an excessive amount of left-to-right shunting would create a deleterious strain on the heart. Too small a cross-sectional diameter at the constriction 409, however, may increase the pressure within the coronary sinus 418 to dangerous levels. Thus, the cross-sectional diameter at the constriction 409 should be large enough to prevent excess pressure build-up, but at the same time be restrictive enough to allow the heart to be supplied with oxygenated blood. For example, the pressure within the coronary sinus 418 does not exceed about 50 mm Hg. In another example, the pressure level within the coronary sinus 418 is preferably about half the systemic pressure level.

Coronary sinus pressure may also be controlled by the amount of blood flowing from the left ventricle 402 into the coronary sinus 418. Thus, the size of the cross-sectional diameter of the arterializing stent 411 may be controlled in relation to the size of the passageway at the constriction 409 to provide efficient retrograde perfusion of heart tissue without excessive pressure build-up.

I claim:

1. A two-piece stent combination for facilitating retrograde supply of oxygenated blood to heart tissue through a coronary sinus comprising:
   an arterializing stent having a leading end configured to be positioned in a left ventricle and a trailing end configured to be positioned in a coronary sinus, and
   a restricting covered stent having an underlying restricting stent and a covering, and having a coronary sinus distal end configured to be positioned in the coronary sinus, and a right atrial proximal end, and exhibiting a constriction between said coronary sinus distal end and said right atrial proximal end.

2. Two-piece stent combination according to claim 1, wherein a cross section of said restricting covered stent tapers toward said constriction.

3. The two piece stent combination according to claim 1, wherein a cross section of said restricting covered stent is appropriately sized to control blood flow from said coronary sinus into right atrium.

4. The two-piece stent combination according to claim 1, wherein said arterializing stent further exhibits a constriction along its length and a cross sectional tapering toward the constriction.

5. The two-piece stent combination according to claim 1, wherein a cross section of said arterializing stent is appropriately sized to control blood flow from said left ventricle into said coronary sinus.

6. The two-piece stent combination according to claim 1, wherein a cross section of said restricting covered stent at said constriction and a cross section of said arterializing stent are appropriately sized to keep pressure inside the coronary sinus from rising above about 50 mm Hg while avoiding excessive left-to-right shunting.

7. The two-piece stent combination according to claim 1, wherein a cross section of said restricting covered stent at said constriction and a cross section of said arterializing stent are appropriately sized to keep pressure inside said coronary sinus from rising above about half systemic pressure.

8. The two-piece stent combination according to claim 1, wherein said restricting covered stent and said arterializing stent allow compression to fit within a delivery catheter.

9. The two-piece stent combination according to claim 1, wherein said restricting covered stent and said arterializing stent allow expansion after delivery.

10. The two-piece stent combination according to claim 1, wherein said arterializing stent and said restricting covered stent are flexible.

11. The two-piece stent combination according to claim 1, wherein said covering of said restricting covered stent is inside underlying restricting stent.

12. The two-piece stent combination according to claim 1, wherein said covering of said restricting covered stent is outside said underlying restricting stent.

13. The two-piece stent combination according to claim 1, wherein said covering of said restricting covered stent partially covers said underlying restricting stent.

14. The two-piece stent combination according to claim 1, wherein said arterializing stent further comprises a covering.

15. The two-piece stent combination according to claim 14, wherein said covering of said arterializing stent is inside arterializing stent.

16. The two-piece stent combination according to claim 1, wherein said arterializing stent is from about 1 cm to about 4 cm in length.

17. The two-piece stent combination according to claim 1, wherein a cross section of said arterializing stent tapers from the trailing end to the leading end.

18. The two-piece stent combination according to claim 17, wherein said trailing end of said arterializing end is from about 4 mm to about 6 mm in diameter and said leading end of said arterializing stent is from about 2 mm to about 5 mm in diameter.

19. The two-piece stent combination according to claim 1, wherein said arterializing stent has a constant cross section.

20. The two-piece stent combination according to claim 19, wherein said arterializing stent is from about 1 mm to about 6 mm in diameter.

21. The two-piece stent combination according to claim 1, wherein said restricting covered stent is from about 1 mm to about 15 mm in diameter.

22. The two-piece stent combination according to claim 1, wherein said constriction of said restriction covered stent is from about 1 mm to about 6 mm in diameter.

23. The two-piece stent combination according to claim 1, wherein said arterializing stent and said restricting covered stent are of mesh construction.

24. The two-piece stent combination according to claim 1, wherein said arterializing stent and said restricting covered stent are of coiled construction.

25. The two-piece stent combination according to claim 1, wherein said arterializing stent and said restricting covered stent are connected.

26. The two-piece stent combination according to claim 2, wherein said right atrial proximal end of said restricting covered stent is positioned within the right atrium.

27. A method for retrogradely supplying oxygenated blood from a left ventricle to heart tissue via a coronary sinus comprising:

puncturing a hole through said coronary sinus and a wall of said left ventricle, delivering an arterializing stent through said hole, wherein a leading end is placed in said left ventricle and a trailing end is placed in said coronary sinus, and delivering a restricting covered stent with a coronary sinus distal end positioned within said coronary sinus.

28. The method according to claim 27, wherein said arterializing stent and said restricting covered stent are delivered percutaneously.

29. The method according to claim 27, further comprising expanding said arterializing stent after delivery within the hole.

30. The method according to claim 27, wherein said constriction of said restricting covered stent is positioned to fit approximately within a coronary ostium.

31. The method according to claim 27, wherein said right atrial end of said restricting covered stent is positioned within a right atrium.

32. The method according to claim 27, wherein said constriction and said right atrial end of said restricting covered stent are positioned within the coronary sinus.

33. The method according to claim 27, wherein said arterializing stent is appropriately sized to control blood flow from said left ventricle into said coronary sinus.

34. The method according to claim 27, wherein said restricting covered stent tapers toward said constriction and is appropriately sized to control blood flow from said coronary sinus into a right atrium.

35. The method according to claim 27, wherein a cross section at said constriction of said restricting covered stent and a cross section at said arterializing stent are appropriately sized to keep pressure inside the coronary sinus from rising above about 50 mm Hg while avoiding excessive left-to-right shunting.

36. The method according to claim 27, wherein a cross sectional at said constriction of said restricting covered stent and a cross section at said arterializing stent are appropriately sized to keep the pressure inside the coronary sinus from rising above about half the systemic pressure.

* * * * *